(12) United States Patent
Miller et al.

(10) Patent No.: US 6,203,486 B1
(45) Date of Patent: Mar. 20, 2001

(54) EARTH MAGNETIC-FIELD AUGMENTERS

(76) Inventors: Wendell E. Miller, 1907 Cresent Dr.; Robert E. South; Michael R. South, both of 1940 Robb Rd., all of Warsaw, IN (US) 46580

( * ) Notice: Subject to any disclaimer, the term of this patent is extended or adjusted under 35 U.S.C. 154(b) by 0 days.

(21) Appl. No.: 09/336,271

(22) Filed: Jun. 18, 1999

Related U.S. Application Data

(60) Provisional application No. 60/135,062, filed on May 20, 1999, provisional application No. 60/126,869, filed on Mar. 30, 1999, and provisional application No. 60/090,842, filed on Jun. 26, 1998.

(51) Int. Cl.[7] ............................. A61B 17/52; A61N 2/00
(52) U.S. Cl. ........................................................ 600/9
(58) Field of Search ................................. 600/9, 13, 14

(56) References Cited

U.S. PATENT DOCUMENTS

| | | |
|---|---|---|
| 5,084,003 * | 1/1992 | Susic ........................................ 600/13 |
| 5,226,185 | 7/1993 | Guay et al. . |
| 5,437,600 * | 8/1995 | Liboff et al. ............................... 600/9 |
| 5,450,859 | 9/1995 | Litovitz . |
| 5,544,665 | 8/1996 | Litovitz et al. . |
| 5,665,049 | 9/1997 | Markoll . |
| 5,788,624 | 8/1998 | Lu et al. . |
| 5,807,233 | 9/1998 | Sakuma et al. . |
| 6,001,055 * | 12/1999 | Souder ........................................ 600/9 |

* cited by examiner

Primary Examiner—Max Hindenburg
Assistant Examiner—Brian Szmal
(74) Attorney, Agent, or Firm—Wendell E. Miller Patent Agent (57) ABSTRACT

Magnetic-field-augmented beds (10, 246, 258, 366, 406, 408, 424, 426), mattresses (330, 352), seating furniture (488), desks (542, 574), carrells (278), railings (514) rooms (168, 202, 216A, 216B), and buildings (156, 164, 192, 230, 472) include magnetic-field augmenters (14, 36, 46, 56, 120, 154, 162, 172, 198, 210, 224A, 224B, 234, 250, 262, 282, 304, 334, 360, 380, 386, 412, 430, 466, 476, 492, 524, 550) that, when connected to a source (70) of electrical power, provide a healthful magnetic field for entire bodies of human beings or other living things in living spaces (31, 182, 300, 507, 531, 549, 591). In another embodiment, a magnetic-field augmenter (444) is hung on a wall (446), and in another embodiment, a magnetic-field augmenter (456) is arranged on a floor (458) around seating furniture (462). Included among the various types of magnetic-field augmenters are bundled augmenter coils (390, 414, 430, 444, 476, 492), two-axis augmenters (492, 550), open-sided augmenters (524, 550), and two-axis open-sided augmenters (550). A protective device (594) protects against loose connections and shorts.

22 Claims, 7 Drawing Sheets

EARTH MAGNETIC-FIELD AUGMENTERS

CROSS-REFERENCE TO RELATED APPLICATIONS

This application claims the benefit of U.S. Provisional Application No. 60/135,062, filed May 20, 1999, U.S. Provisional Application No. 60/126,869, filed, Mar. 30, 1999, and U.S. Provisional Application No. 60/090,842, filed Jun. 26, 1998.

STATEMENT RE FEDERALLY SPONSORED RESEARCH OR DEVELOPMENT

Not Applicable

REFERENCE TO A "MICROFICHE INDEX"

Not Applicable

BACKGROUND OF THE INVENTION

1. Field of the Invention

The present invention relates generally to magnetic fields. More particularly, the present invention relates to apparatus and method for augmenting the earth's magnetic field in living spaces for work, sleep, and/or play, for general enhancement of health and medical therapy, and for long-term whole-body magnetic therapy.

2. Background Art

The importance of D.C. magnetic fields to all living cells is well known. In addition, there is an abundance of medical literature that convincingly proves the therapeutic value of D.C. magnetic fields to heal bones and to relieve muscle soreness.

Permanent magnets have been used singularly as shoe insoles, they have been used as bracelets and necklaces, and large numbers of magnets have been distributed over large areas to provide magnetic blankets. While the use of magnets as bracelets and necklaces would seem to be folklore, there is abundant evidence that D.C. magnetic fields do accelerate bone healing.

Included in the many patents on magnetic-field therapy, commonly referred to as biomagnetics, is Markoll, U.S. Pat. No. 5,665,049, issued Sep. 9, 1997. Although the use of permanent magnets applied to the body has been proven to promote bone healing, a question remains: what happens to cell communication at locations, adjacent to the permanent magnets, in which the magnetic force of the magnet cancels the beneficial effects of the earth's magnetic field.

Guay et. al., U.S. Pat. No. 5,226,185, issued Jul. 13, 1993, teaches the use of a plurality of magnetic strips that are disposed in longitudinal and parallel spaced-apart rows under a quilted top and a foam layer of a mattress. Even if each magnetic strip had only two poles, the result would be a sleeping surface with a relatively large number of poles. Therefore, it would appear that the user's body would be subject to magnetic fields that would, at various places in his body, cancel the earth's magnetic field and its beneficial effects.

Sakuma et al., in U.S. Pat. No. 5,807,233, issued Sep. 15, 1998, also teach applying permanent magnets to aching portions of a person's body. They report cases in which patients having arthritis and osteoarthritis found relief in magnetic therapy.

While the known temporary medical benefits of permanent magnet therapy for relief of muscle pain, accelerated bone healing, and relief of arthritis pain may outweigh any negative effects, subjecting a human body to a large number of magnetic-field deficient sites for a long period of time, as must be the situation with blankets that use a large number of permanent magnets, may be harmful.

QRS America offers a pad upon which a person may lie, and be subjected to magnetic-field therapy that is defined as, "quantron resonance therapy using pulsed magnetic fields operating at a range of frequencies." More information is available from QRS America, 2321 Sandlewood Drive, Venice, Fla. 34293.

There is considerable evidence that A.C. magnetic fields, particularly in the 50 and 60 Hertz frequencies generally used in homes and industry, hamper proper cell communication. Convincing evidence is available on the Internet from EMF-Link of Information Ventures, Inc., 425 South 15th Street, Suite 700, Philadelphia, Pa. 19102, regarding the harmful effects of A.C. magnetic fields.

Dr. Neil Cherry, a New Zealand researcher, states that tests on breast cancer cells prove that A.C. magnetic fields in the range of 2.0 to 12.0 milligauss cancel the oncostatic effect of melatonin.

Alternating-current magnetic fields have also been connected with an increase of almost four times in Alzheimer's disease among workers who use industrial sewing machines, as reported by E. Sobel and his associates in two articles published in Neurology magazine.

In contrast, as reported in the Online Edition of the Dallas/Ft. Worth Heritage, May, 1998, Volume 6, Number 11, tests conducted by the Creation Evidences Museum in Glen Rose, Tex., in an environment free from A.C. magnetic fields and their debilitating effects and also exposed to a D.C. magnetic field of 5.0 gauss, resulted in extending the life of fruit flies. It is believed that the researcher was Dr. Carl E. Baugh, director of the museum.

While much work has been done with regard to magnetic-field healing, very little has been done to overcome the harmful effects of A.C. magnetic fields, and thereby to provide a more healthful environment. However, Litovitz et al., in U.S. Pat. No. 5,544,665, issued Aug. 13, 1996, seeks to overcome the harmful effects of A.C. magnetic fields by superimposing a pulsating D.C. field onto A.C. magnetic fields.

It is well-known that the earth's magnetic field is decreasing, and that it is decreasing exponentially, as a function of "e" to a negative exponent that consists of a time multiplied by a constant.

Therefore, it is logical to assume that the earth's magnetic field is now of a lower magnitude than that which would provide optimum health. Further, the magnitude of the earth's magnetic field varies regionally, and so it is even further reduced from a healthful optimum in some geographical areas.

Knowing that the earth's magnetic field is essential to cell communications, knowing that this beneficial field has decreased from an earlier optimum-health magnitude, knowing that the magnitude of the earth's magnetic field is even lower in some geographical areas, and believing that A.C. magnetic fields are harmful, which seems to be well proven, it is hypothesized herein that one way to overcome, or at least minimize, the harmful effects of A.C. magnetic fields is to augment, or supplement, the earth's D.C. magnetic fields in living spaces used for such activities as work, recreation, and sleep.

That is, if a certain magnitude of a D.C. magnetic field is necessary for healthful cell communications, then when an A.C. magnetic field happens to be oriented substantially in line with the earth's magnetic poles, then the summed A.C. and D.C. fields may produce a fluctuating D.C. field in which the minimum magnitude may not be sufficient for healthful cell communication.

Unfortunately, researchers into the deleterious effects of A.C. magnetic fields may not have considered either the three-axis relationship of A.C. magnetic fields to the earth's magnetic field or regional differences in magnitude of the earth's magnetic field. Hopefully, future researchers will consider not only the three-axis relationship of A.C. fields to the earth's magnetic poles, but also regional variations of the earth's magnetic field.

Knowing that increased levels of D.C. magnetic fields are beneficial, providing a D.C. magnetic field at any three-axis orientation that adds to the earth's magnetic field should be beneficial to health. That is, the trigonometrically-summed D.C. field will be of greater magnitude than the earth's magnetic field, alone.

Therefore, when human or animal life is subjected to A.C. magnetic fields, and these A.C. magnetic fields are trigonometrically-summed with the trigonometrically-summed magnitude of the earth's magnetic field and an augmenting D.C. magnetic field, the minimum D.C. magnetic field will be of sufficient strength to provide for healthful cell communications.

Whether augmenting the earth's magnetic field with an other D.C. magnetic field will obviate the detrimental effect of A.C. magnetic fields on the action of Melatonin is yet to be proven. However, based on the beneficial effects of higher magnetic fields on fruit flies in a controlled environment, as mentioned above, it appears certain that the magnetic field augmenters of the present invention will provide a more healthful environment, even it they do not overcome all of the detrimental effects of A.C. magnetic fields.

Therefore, if the entire body of a person, or the entire bodies of a group of people, animals, and/or plants are totally immersed for extended periods, preferably for a number of hours each day, in a D.C. magnetic field provided by one of the magnetic-field augmenters of the present invention, the health benefits should be substantial and much greater than scanning the body with a D.C. magnetic field as taught by Lu et al. in U.S. Pat. No. 5,226,185.

Since healthful cell communications are critical in life processes, it may be that magnetic-field-augmented living spaces will help prevent some cancers, although this is yet to be proven. However, the use of food additives, hormones in animal growth, insecticides, pesticides, and other chemicals make it seem extremely unlikely that an augmented magnetic field will prevent all cancers.

On the other hand, it may be that living spaces with higher-gauss augmentation may help cure some cancers. It should be understood that, as defined herein, if a patient is living in a hospital bed, and an augmented magnetic field is supplied above his mattress, he is living in a magnetic-field-augmented living space.

Furthermore, just as it has become common medical procedure to provide supplementary oxygen to seriously-ill patients, there may come a day when it is equally common to provide relatively long-term, and whole-body, magnetic therapy as taught herein, either separately, or together with supplementary oxygen.

In summary, in the present invention, various magnetic-field-augmented apparatus and various magnetic-field augmenters are taught herein wherein an entire human body, or that of any other living thing, may be subjected to an augmented magnetic field of as low as 1.0 gauss for a number of hours each day for maintenance of health, or to a considerably higher level of D.C. magnetic fields for days at a time for treatment of disease.

Although a major thrust of the present invention is augmenting the earth's D.C. magnetic field, when the present invention is practiced for therapy, and the body is exposed to higher gauss levels, the present invention is characterized as providing living spaces for wholebody immersion into a magnetic field, whether or not the earth's magnetic field is excluded, and whether or not supplementary oxygen is included in therapy.

SUMMARY OF THE INVENTION

Apparatus and method are provided for immersing a living thing in its entirety, whether it be an entire human body, an entire body of an animal, an entire plant, or any other living thing in its entirety, into a living space with a healthful magnetic field that augments the earth's magnetic field, for extended periods of time such as during working hours, recreation, sleep, and/or living-space application of whole-body magnetic therapy.

Each type of magnetic-field-augmented apparatus, as taught herein, includes a magnetic-field augmenter. When a magnetic-field augmenter is combined with a structure, the combination becomes a magnetic-field-augmented apparatus.

Preferably, a D.C. magnetic field, whose time-weighted average exceeds 1.0 gauss, is used for this healthful field, whether constant or varying. However, apparatus taught herein may be used with any magnetic field that may, in the future, be proved to be healthful, including pulsating D.C., A.C. or a combination of D.C. and A.C., to practice the present invention.

The present invention may be used to produce higher magnitudes of magnetic flux in living spaces, or therapy spaces, for immersion of a living thing in its entirety for extended periods of time, such as hours, days, or weeks for intensive magnetic therapy of patients who are seriously or critically ill.

A magnetic-field-augmented living space (MFA livingspace), as defined herein, is any place in which an area is magnetic-field augmented to a height that will envelope a human, an animal, an other living thing, or a number of living things, in which a human, an animal, or an other living thing normally resides for a period of time for a purpose other than magnetic-field augmentation or therapy, and in which normal use of the living space by the human, animal, or other living thing continues a normal activity during times when the earth's magnetic field is augmented in the living space.

As taught herein, magnetic-field-augmented living spaces may include entire floor areas, or partial floor areas of houses, buildings, factories, rooms in houses, hospital or nursing home rooms, offices, barns, animal trailers, animal housing, animal retaining areas, hatcheries, incubators, greenhouses, and any other structure that may be used for a living space for any living thing.

Further, magnetic-field augmented spaces may include work carrells, TV carrells, carrells for hospital and nursing-home patients, and any other space in which a healthful magnetic field is added, in which the primary use for the living space is other than exposure to a healthful magnetic field, and in which the primary use for the living space is continued during exposure to healthful magnetic fields. In addition, magnetic-field-augmented living spaces may be disposed above sleeping areas of beds in homes, nursing homes, and hospitals.

A magnetic-field therapy space (MF therapy space), as opposed to a magnetic-field-augmented living space, as defined herein, is a place in which a patient is placed, or places himself, especially, if not exclusively, for magnetic therapy.

A house that is advertised as air-conditioned may not yet be connected to a source of electrical power; even so, a magnetic-field-augmented apparatus as defined herein does not include a source of electrical power.

Each type of magnetic-field-augmented apparatus includes a magnetic-field augmenter. For instance, a magnetic-field-augmented house includes a magnetic-field augmenter; and a magnetic-field-augmented bed includes a magnetic-field augmenter.

A magnetic-field augmenter may consist of a multi-turn augmenter coil that is disposed in a particular place for the purpose of augmenting the earth's magnetic field. Or, a magnetic-field augmenter may include some structure in addition to a multi-turn augmenter coil.

For instance, a magnetic-field augmenter for a bed may be made by winding multiple-turns of wire around grooves in a bed structure. In this case, the magnetic-field augmenter consists of a multi-turn augmenter coil that is disposed around a bed to provide a particular function.

Alternately, a magnetic-field augmenter for a bed may include a multi-turn augmenter coil, some kind of structure for retaining the turns of the multi-turn augmenter coil, and some kind of structure, such as straps, for positioning he multi-turn augmenter coil with respect to a sleeping area.

In preferred embodiments, magnetic-field augmenters of the present invention provide an augmenting D.C. magnetic field and comprise a multi-turn augmenter coil that surrounds, or partially surrounds, a living space, or that surrounds, or partially surrounds, an area projected from a living space.

For instance, if a magnetic-field augmenter is disposed around a perimeter of a mattress, then it surrounds an area that is projected downward from a sleeping area of the mattress, and the living space is disposed above the sleeping area. Further, in magnetic-augmenters for work carrells or TV carrells, if only three walls are used, and one side is left open, then the magnetic-field augmenter partially surrounds the magnetic-field augmented living space.

Preferably, multiple-turn coils are made of round wire or flat strips of conductive material such as aluminum or copper. The turns may be closely juxtaposed, spaced apart, or bundled, as taught herein.

When flat strips are used, the strip material may be as narrow as an inch, or less, and as wide as 25.5 cm. (10 inches), and the thickness of the strips may be no more than 0.25 mm. (0.01 inches) or as much as 3.18 mm. (0.125 inches). Turns may be spaced apart as much as 25.4 mm. (1.0 inches). Voltages applied to the coils may be as low as 2.0 volts or as large as is obtainable by rectifying A.C. house voltages.

In a first aspect of the present invention, a method for providing a magnetic-field-augmented living space comprises: providing a living space having a length, a width, and a height; and supplementing earth's magnetic field in the living space with an other healthful magnetic field.

In a second aspect of the present invention, a method for healthful living comprises: disposing one's entire body into a living space having a length, a width, and a height; supplementing earth's magnetic field in the living space with an other healthful magnetic field; and performing a life activity in the living space during the supplementing step.

In a third aspect of the present invention, a method for supplementing earth's magnetic field as an integral part of normal sleep comprises: providing a bed having a mattress with a living space above a top surface, the living space having a length, a width, and a height that is sufficient to envelop a person lying on the mattress; and supplementing the earth's magnetic field in the living space with an other healthful magnetic field during at least a period of time wherein the bed is used for normal sleep.

In a fourth aspect of the present invention, a method for applying a supplementary magnetic field to a living thing comprises: providing a living space; disposing the living thing into the living space; retaining the living thing in the living space for a period of time that exceeds four hours; and supplementing earth's magnetic field in the living space with an other healthful magnetic field for a predetermined period of time.

In a fifth aspect of the present invention, a method for magnetic-field augmenting a living space of a bed, the bed having a mattress with four edges, and with the living space being disposed above a sleeping surface of the mattress, comprises: disposing an augmenter coil in a pattern that generally conforms to the edges; and supportingly positioning the augmenter coil with respect to the sleeping surface.

In a sixth aspect of the present invention, a method for providing a magnetic-field-augmented living space that is relocatable comprises: disposing a free-standing support around a portion of a perimeter of a selected living space; leaving an access opening between ends of the free-standing support; and disposing an augmenter coil along the free-standing support.

In a seventh aspect of the present invention, a method for magnetic-field augmenting a living space comprises: generating an augmenting magnetic field; generating a first portion of the augmenting magnetic field with poles that are disposed along a first axis; and generating a second portion of the augmenting magnetic field with poles that are disposed along a second axis that is orthogonal to the first axis.

A first object of the present invention is to provide apparatus and method for supplementing the earth's magnetic field in a living space for work, sleep, relaxation and/or play.

A second object of the present invention is to provide apparatus and method for increasing the beneficial effects of the earth's D.C. magnetic field for a living thing in a living space.

A third object of the present invention is to provide apparatus and method for overcoming the debilitating effects of A.C. magnetic fields by superimposing a D.C. magnetic field that can be applied to living spaces, such as work, sleep, rest, and recreational living spaces.

A fourth object of the present invention is to provide apparatus and method for providing healthful D.C. magnetic fields in a living space that so abundantly exceed unhealthy A.C. magnetic fields that eight hours in an augmented field will overcome the detrimental effects of A.C. magnetic fields during the remainder of a day that a person, an animal, or an other living thing may be outside the magnetic-field-augmented living area.

A fifth object of the present invention is to provide apparatus and method for use in providing entire-bodyengulfing magnetic fields for use in intensive human and animal biomagnetic therapy.

DESCRIPTION OF THE PREFERRED EMBODIMENTS

Figure 1:
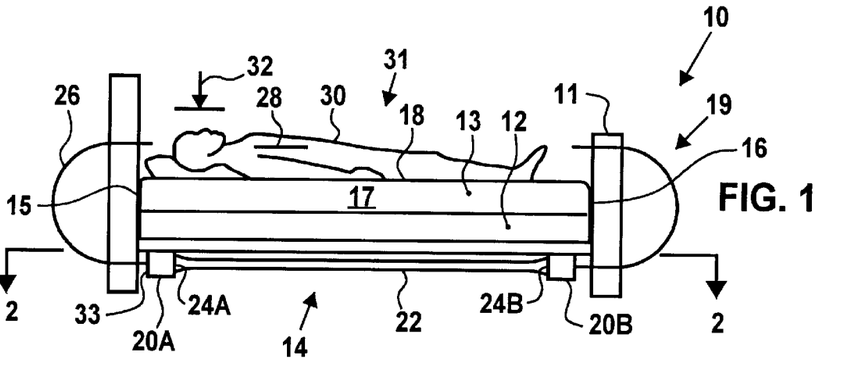
FIG. 1 is a side elevation of magnetic-field-augmented bed with permanent-magnet augmenters disposed under the bed structure.

Referring now to FIG. 1, a magnetic-field-augmented bed, or magnetic-field augmented apparatus, 10 includes a bed, or bed structure, or furniture structure, 11, a box spring 12, a mattress 13, and a plurality of magnetic-field augmenters 14. The mattress 13 includes a head edge 15, a foot edge 16, and a pair of side edges 17 that depend downwardly from a top surface, or sleeping surface 18, and that form a perimeter 19 around the mattress 13.

Each of the magnetic-field augmenters 14 includes permanent magnets 20A and 20B and a magnetic flux guide 22 that is superimposed between, and juxtaposed against, the magnets 20A and 20B. Therefore, even though the magnets 20A and 20B generate opposite poles on ends 24A and 24B of the flux guide 22, a resultant magnetic field 26 is produced approximately as shown. The magnetic-field augmenters 14 are designed to produce a magnetic field with a magnitude of 0.5 to 5.0 gauss along a magnetic flux line 28 that passes through a person, or body of a human, 30. More particularly, the magnetic-field augmenters are designed to augment a living space 31 that extends upwardly for a height 32 from the top surface 18 that is sufficient to engulf a body of a human 30. Obviously, the edges 15, 16, and 17 define a length, not numbered, and a width, not numbered, of the living space 31.

Preferably, the magnetic-field augmenters 14 are longitudinally-disposed, as shown, although transversely-disposed magnetic-field augmenters may be advantageous in some situations.

North poles 33 of the magnetic-field augmenters 14 are aligned to supplement the earth's magnetic field, at any three-axis relationship, but preferably not at an angle wherein the augmenter will cancel or replace the earth's magnetic field. For instance, if the augmenters 14 produced a magnetic field of 4.5 gauss that supplements the earth's magnetic field, the beneficial D.C. magnetic field would be increased by a factor of 10.0.

Figure 2:
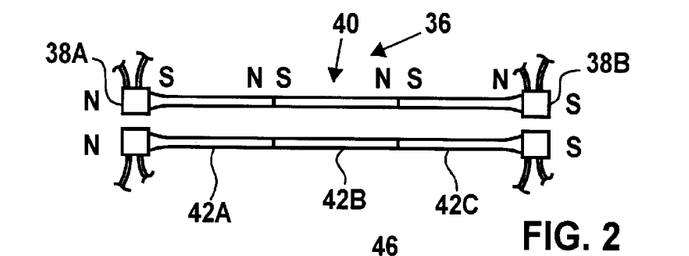
FIG. 2 a top view of electromagnet augmenters that optionally replace the permanent-magnet augmenters of FIG. 1, taken substantially as shown by view line 2—2, with the augmenters being built in sections to facilitate shipment.

Referring now to FIG. 2, magnetic-field augmenters 36 may be substituted for the magnetic-field augmenters 14 in the magnetic-field-augmented bed 10 of FIG. 1.

Each of the magnetic-field augmenters 36 includes a pair of electromagnets 38A and 38B and a magnetic flux guide 40 that is similar to the magnetic flux guide 22 of FIG. 1, except that the magnetic flux guide 40 is segmented into three parts 42A, 42B, and 42C to facilitate shipment. Application of a D.C. voltage to the electromagnets 38A and 38B from a source, not shown, produces north and south poles, as shown.

The three parts, 42A, 42B, and 42C are fixedly juxtaposed by any suitable means, not shown, not an inventive part of the present invention. Since the magnetic flux guide 40 is segmented into three parts, north and south poles are generated, as shown.

Figure 3:
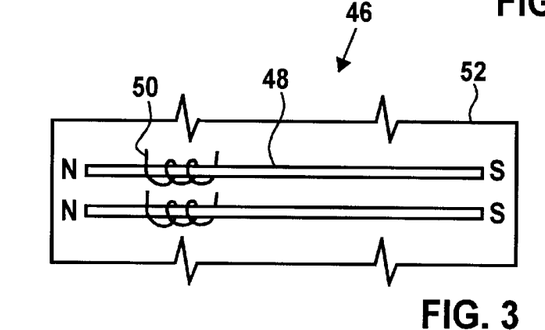
FIG. 3 is a top view of an electromagnetic augmenter, taken substantially the same as FIG. 2, which may be used with the bed structure of FIG. 1 to replace the magnetic-field augmenters of FIG. 1.

Referring now to FIG. 3, a magnetic-field augmenter 46 includes a plurality of parallel magnetic cores 48, each being wound with a coil 50, and all being enclosed between a pair of welded sheets 52 of plastic. Application of a D.C. voltage to the coils 50 from a source, not shown, produces north and south poles, as shown. The augmenter 46 may be rolled, boxed, and shipped within acceptable parcel size limits.

Figure 4:
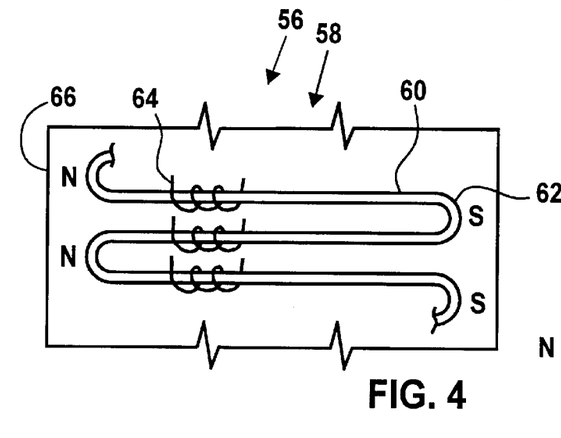
FIG. 4 is a top view of an electromagnetic augmenter, taken substantially the same as FIG. 2, which utilizes a serpentine magnetic core, and which may be used with the bed structure of FIG. 1 to replace the augmenters of FIG. 1.

Referring now to FIG. 4, a magnetic-field augmenter 56 includes a serpentine magnetic core 58 of magnetic material. The serpentine magnetic core 58 includes a plurality of rod portions 60 and a plurality of curved connecting portions 62. As shown, each of the rod portions 60 is wound with a coil 64.

The coils 64 are wound onto a length of magnetic material, not shown, that is subsequently bent into the serpentine magnetic core 58; and the serpentine magnetic core 58, complete with coils 64, is welded between a pair of plastic sheets 66. Application of a D.C. voltage to the coils 64 from a source, not shown, produces north and south poles, as shown, in the curved connecting portions 62.

Referring now to FIGS. 3 and 4, preferably, the magnetic-field augmenters, 46 and 56, are relatively flexible so that they can be placed between the mattress 13 and the box spring 12 of FIG. 1, as well as being placed under a mattress of a water bed (not shown) or under the bed structure 11 of FIG. 1.

The flux-guides 22 and 40, and the cores 48 and 58, may be made from material that is more economical than is needed for permanent magnets, and also more economical than is needed for electromagnets. That is, these applications do not require a material that will retain its magnetism for an extended length of time as do permanent magnets, nor do they require a material, such as soft iron, in which magnetic poles can be reversed rapidly without a high energy loss.

Figure 5:
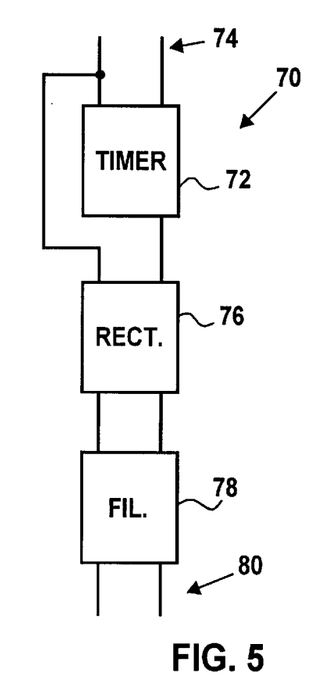
FIG. 5 is a block diagram of a power supply that is applicable to any of the embodiments of the present invention that use electrical power to develop an augmenting magnetic field.

Referring now to FIG. 5, a power source, or source of electrical power, 70, that may be used with any of the various magnetic-field augmenters and/or magnetic-field-augmented apparatus of the present invention, includes a timer 72 that is connected to A.C. input conductors 74, a full-wave rectifier 76, a filter 78, and output conductors 80.

Figure 6:
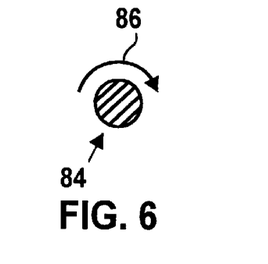
FIG. 6 is a cross section of a wire carrying a current that is flowing downward into the paper, showing a magnetic field that is developed thereby.

Referring now to FIG. 6, a wire 84 is shown in cross section. If a current is flowing downward through the wire 84 into the paper, the current flow through the wire 84 develops magnetic flux in the direction shown by an arrow 86. With the thumb of the right hand in the direction of current flow, the direction of the magnetic flux around the wire is in the direction of fingers of the right hand.

Figure 7:
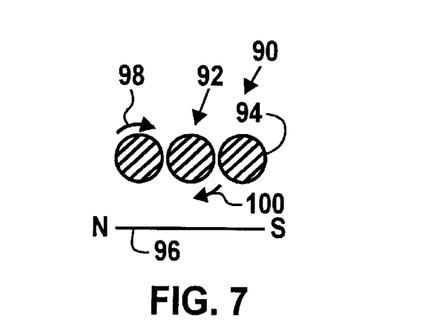
FIG. 7 is a cross section of a multi-turn augmenter coil with a longitudinal axis disposed below the cross-sectioned coils, and with current flowing downward into the paper, showing magnetic flux and magnetic poles developed thereby.

Referring now to FIG. 7, a multi-turn augmenter coil 90, which may be used as an augmenter coil, is shown in cross section, and includes a plurality of turns 92 of wire 94 that are wound around an axis 96. If current is flowing downwardly through the turns 92 of wire 94 into the paper, magnetic flux flows generally as shown by an arrow 98, and develops north and south magnetic poles as shown, but some magnetic flux flows between coils, as shown by an arrow 100.

With fingers of the right hand pointing in the direction of current flow through the turns 92 of wire 94, the thumb points toward the north pole.

Figure 8:
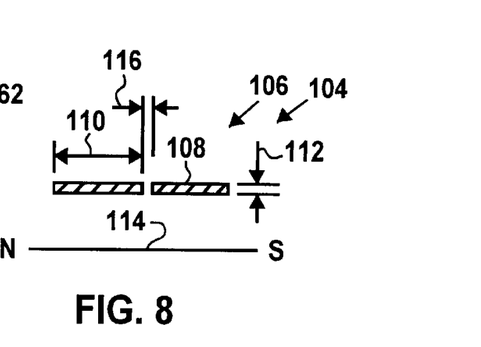
FIG. 8 is a cross section of a multi-turn augmenter coil formed from relatively wide and relatively thin strips, a longitudinal axis of the coil being disposed below the cross-sectioned coils, and current flowing downward into the paper, showing magnetic poles developed thereby.

Referring now to FIG. 8, a magnetic-field augmenter, or multi-turn augmenter coil, 104 is shown in cross section, and includes a plurality of turns 106 of conductive strip 108 having a width 110 and a thickness 112, that are wound around an axis 114 with an adjacent gap 116 between the turns 106. North and south magnetic poles are generated, as shown.

Figure 9:
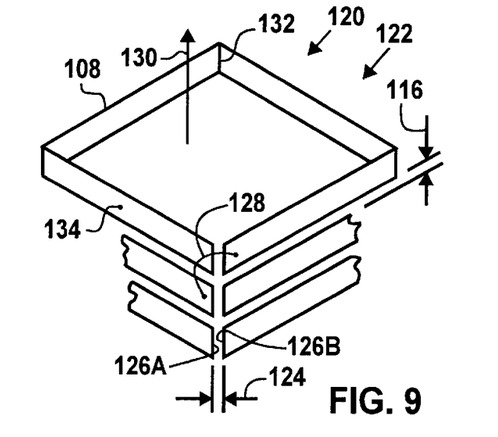
FIG. 9 is a partial and perspective view of a magnetic-field augmenter in which non-pitched turns, consisting of strips of conductive metal, are connected in series by the use of jumpers, thereby forming a magnetic-field augmenter.

Since magnetic-field augmenters, or multi-turn augmenter coils of the present invention may have a length of about 0.46 meters (18 inches) long to perhaps 5.2 meters (17 feet) long, rectangular material such as is shown in FIG. 9, may be useful for winding the magnetic-field augmenters.

It might be supposed that overlapping strip material, much as shingles of a house are overlapped, would decrease flux loss between coils. However, tests have determined that, for gauss densities of 5.0 gauss, or less, adjacent gaps 116 of FIG. 8 may be as much as 2.54 mm. (1.0 inches) without undue loss of magnetic flux between turns 92 of FIG. 7, or turns 106 of FIG. 8, whether round or flat conductors are used.

Therefore, use of rectangular strips does not necessarily provide a substantial advantage, unless the augmenter coil is very long. However, for surrounding a two-story house, an augmenter coil may have a length, which is the vertical dimension, of about 5.18 meters (17 feet). The strips 142 may be 5.08 cm. (2.0 inches) wide and 3.2 mm. (0.125 inches) thick, or they may be 22.9 to 25.4 cm (9 to 10 inches) wide and only 0.25 mm (0.10 inches) thick. However, as will be shown later, the augmenter coil length does not necessarily need to be equal to ceiling height of a room, standing height for individuals, or even sitting height.

Referring now to FIG. 9, a magnetic-field augmenter, or multi-turn augmenter coil, 120 includes a plurality of individual, rectangularly-shaped turns 122 made from conductive strips 108 with end gaps 124 that prevent individual turns 122 from shorting themselves. The strips 108 include widths 110 and thicknesses 112 as shown in FIG. 8. Adjacent gaps 116 may be minimized or spread apart as previously discussed.

Preferably, an end 126A of each individual turn 122 is connected to an end 126B of an other individual turn 122 by means of a jumper 128, thereby providing the magnetic-field augmenter 120 which is non-pitched. Optionally, all of the ends 126A may be connected together, and all of the ends 126B may be connected together, to form a low-voltage high-amperage augmenter, not shown. North and south poles are disposed along an axis 130.

The strips 108 and may be as wide as 22.0 cm. (9 inches), or more, and adjacent gaps 116 may be small. However, round wire may be used, and whether round wire or strips are used, spacings between coils may be relatively large, as taught above. If the strips 108 are too rigid to be formed at corners 132, or if an individual strip 108 is shorter than a side 134, they may be electrically connected by any suitable means, such as the jumper 128.

Figure 10:
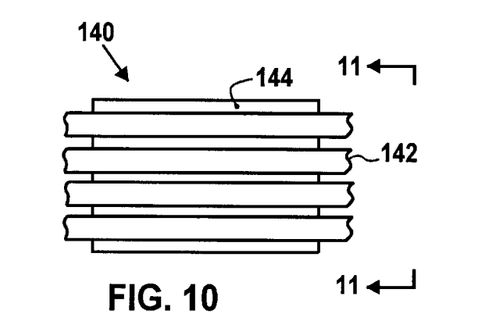
FIG. 10 is a partial plan view of an augmenter-coil wrap in which strips of conductive material are bonded to a non-conductive backing, which may be used to construct a magnetic-field augmenter for a bed, which may be used inside a room before application of sheetrock, or which may be used for wrap around a building, either under or over sheeting, for clarity showing the strips extending from ends of the non-conductive backing.
Figure 11:
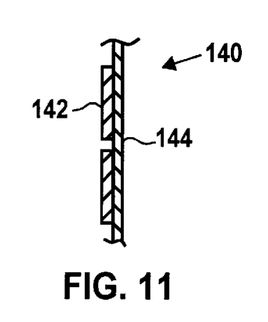
FIG. 11 is an enlarged partial view of the augmenter-coil wrap of FIG. 10 taken substantially as shown by view line 11—11 of FIG. 10.

Referring now to FIGS. 10 and 11, augmenter coil wrap 140 includes a plurality of strips 142 of conductive material that are spaced apart, and bonded to a non-conductive backing 144. The augmenter-coil wrap 140 can be used in place of plastic wrap that is often used over sheeting in building construction, it can be used under sheetrock, or it can be used for making smaller magnetic-field augmenter coils, as will be discussed subsequently.

Preferably, the strips 142 are of copper, thereby providing both good conductivity and excellent soldering qualities for interconnection of jumpers, such as the jumpers 128 of FIG. 9.

Figure 12:
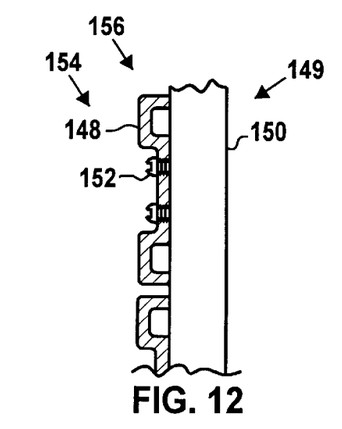
FIG. 12 is cross-section of aluminum-strip sheeting attached to a portion of a stud of a building, thereby providing a magnetic-field-augmenter when interconnected as shown in FIG. 9, whether used on the outside of a building under plastic siding, or used inside a room under any suitable covering.
Figure 16:
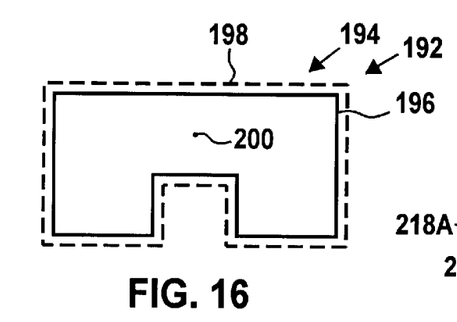
FIG. 16 is a schematic top view of a magnetic-field-augmented building, showing a magnetic-field augmenter that is perimetrically disposed, as symbolized by a dash line.

Referring now to FIG. 12, sheeting strips 148 are rolled from aluminum sheet, or extruded from aluminum stock, preferably about 0.51 mm. (0.02 inches) thick. The sheeting strips 148 are disposed perimetrically around a building, or building structure 149 of FIG. 12, as shown in FIG. 16. The sheeting strips 148 may be attached directly to studs 150 using screws 152, or by any other suitable means, and may replace conventional sheeting.

When interconnected with jumpers 128, as shown in FIG. 9, a magnetic-field augmenter, or multi-turn augmenter coil, 154 is formed around the building 149 of FIG. 12, as shown in FIG. 16, and the resultant apparatus is a magnetic-field-augmented apparatus, or magnetic-field-augmented building 156.

The natural color of the aluminum serves as reflective insulation. Plastic siding, not shown, or bricks, not shown, may be used over the sheeting strips 148, not an inventive part of the present invention.

Figure 13:
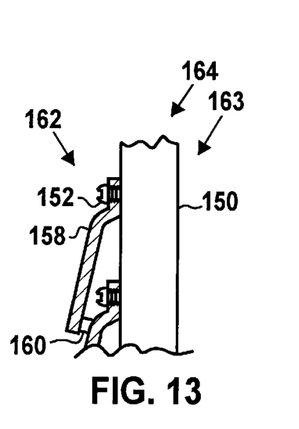
FIG. 13 is a cross-section of aluminum siding which may be used with sheeting, or used without sheeting and fastened directly to studs, as shown, and when interconnected as shown in FIG. 9, provides a magnetic-field augmenter.

Referring now to FIG. 13, aluminum siding 158 functions as a coil strip, is preferably about 0.51 mm. (0.02 inches) thick, and is attached directly to the studs 150 using the screws 152, or by any other suitable means, thereby obviating the cost of sheeting, not shown. Foam rubber strips 160 with self-stick surfaces provide stability and electrical spacing between adjacent pieces of the aluminum siding 158 as well as preventing access to insects.

When interconnected with jumpers 128, as shown and described in conjunction with FIG. 9, or by any other suitable means, a magnetic-field augmenter, or multi-turn augmenter coil, 162 is provided that may extend around a building, or building structure, 163 of FIG. 13, such as is shown in FIG. 16, the resultant apparatus is a magnetic-field-augmented apparatus, or magnetic-field-augmented building 164.

Figure 14:
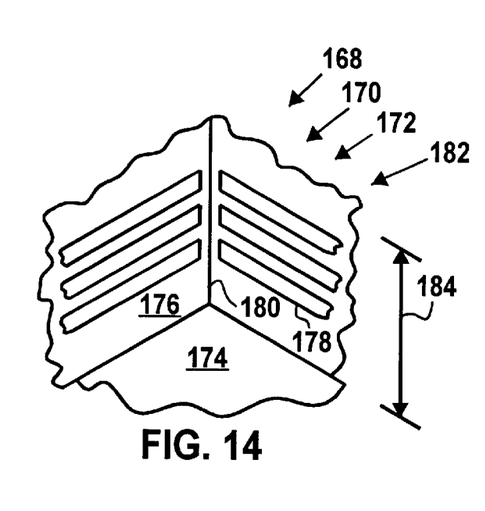
FIG. 14 is a partial perspective view in which strips of conductive material are wallpapered inside a room of an existing building which, when connected as shown in FIG. 9, provides a magnetic-field augmenter.

Referring now to FIG. 14, magnetic-field-augmented apparatus, or a magnetic-field-augmented room, 168 includes a room, or room structure, 170 and a magnetic-field augmenter, or multi-turn augmenter coil, 172. The room 170 includes a floor 174 and interior wall surfaces 176. Strips 178 of conductive material are wallpapered onto the interior wall surfaces 176, and are continuous around corners, as shown in FIG. 9, except for one corner 180, and except as will be discussed in conjunction with FIG. 15. When the strips 178 are connected with jumpers 128, as shown in FIG. 9, the magnetic-field augmenter 172 is formed, thereby providing the magnetic-field-augmented room 168.

If the magnetic-field-augmented room 168 is to be used primarily for persons who will be sitting or sleeping, a magnetically-augmented living space 182 does not necessarily need to extend to a height 184 that is more than 1.5 meters (5.0 feet) above the floor 174. And, since the magnetic-field-augmented living space 182 will extend both above and below the magnetic-field augmenter 172, the magnetic-field augmenter does not need to be a long as the height 184.

In like manner, a living space in any building does not necessarily need to extend up to a ceiling of the building, a magnetic-field augmenter thereof does not necessarily need to extend down to a floor, and the magnetic-field augmenter does not necessarily need to extend upwardly to a height of a magnetic-field-augmented living space.

However, if a magnetic-field augmenter extends around a room, a building, or another defined area, a magnetically-augmented living space includes both an area surrounded by the magnetic-field augmenter and a height that is sufficient to engulf the particular living thing placed therein.

Referring again to FIGS. 12, 13, and 14, as taught in conjunction with FIG. 9, the strips, 148 or 158, may be connected to provide a low-voltage high-current augmenter, not shown.

Figure 15:
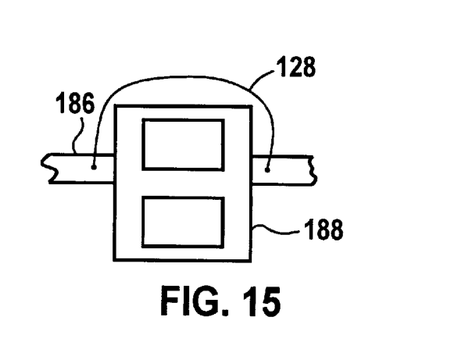
FIG. 15 is a partial elevation showing a window and jumpering across a window opening to respective ones of the sheets of sheeting or siding of FIGS. 12 or 13.

Referring now to FIG. 15, jumpers 128, one shown, interconnect respective ones of augmenter coil strips 186 that are spaced apart by a wall opening, or window, 188 in the constructions shown and described in conjunction with FIGS. 12–19 and 36.

Referring now to FIG. 16, magnetic-field-augmented apparatus, or a magnetic-field-augmented building, 192 includes a building, or a building structure, 194 with a structural perimeter 196, and a magnetic-field augmenter, or multi-turn augmenter coil, 198, as symbolized by dash lines.

The magnetic-field augmenter 198 of FIG. 16 is applied perimetrically, inside or outside of the studs 150 of FIGS. 12 and 13, by any suitable means, and interconnected as shown and described in conjunction with FIGS. 9 and 15, or by any suitable means. The magnetic-field augmenter 198 produces poles along an axis 200.

Figure 17:
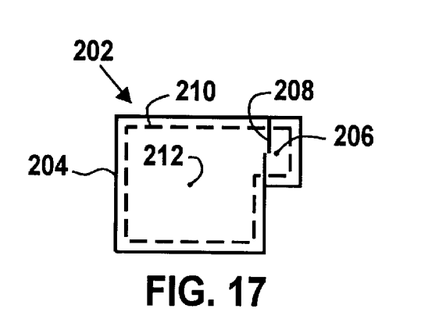
FIG. 17 is a schematic top view of a room, showing a magnetic-field augmenter around an inside thereof and around an inside of a closet.

Referring now to FIG. 17, magnetic-field-augmented apparatus, or a magnetic-field-augmented room, 202 includes a room, or room structure 204, having a closet 206 and closet doors 208, includes a magnetic-field augmenter, or multi-turn augmenter coil, 210 that is depicted by a dash line. The magnetic-field augmenter 210 encloses both the room 204 and its closet 206, as shown. The magnetic-field augmenter 210 may be constructed as shown and described in conjunction with FIGS. 9–15 or 36, or by any other suitable means. The magnetic-field augmenter 210 produces north and south poles along an axis 212.

Figure 18:
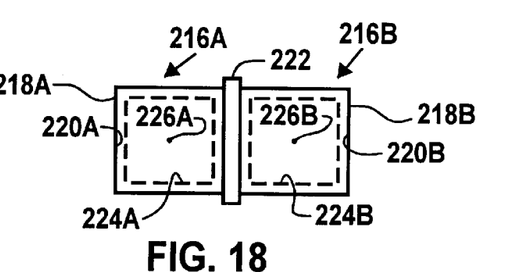
FIG. 18 is a schematic top view of adjacent rooms, with inside-wall surfaces separated by studs, showing a pair of adjacent and magnetic-field augmenters that are perimetrically disposed around respective ones of the rooms, as symbolized by dash lines.

Referring now to FIG. 18, magnetic-field-augmented apparatus, or magnetic field augmented rooms 216A and 216B include rooms, or room structures, 218A and 218B, with wall surfaces, 220A and 220B, that are separated by a stud structure 222. Each of the rooms, 218A and 218B, includes a magnetic-field augmenter, or multi-turn augmenter coil, 224A and 224b, as indicated by a dash line on respective ones of the wall surfaces, 220A and 220B, and juxtaposed to opposite sides of the stud structure 222.

Applying a potential to the magnetic-field augmenters, 224A and 224B generates magnetic fields with north and south poles that are oriented along axes 226A and 226B. With the same directions of current flow, the magnetic fields of both of the magnetic-field augmenters, 224A and 224B, complement each other. However, opposite polarities may be used.

Figure 19:
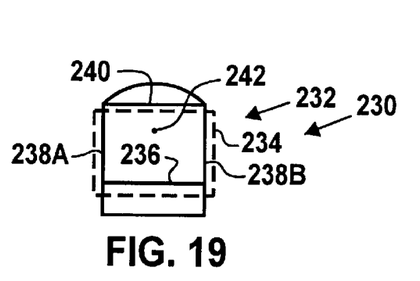
FIG. 19 is an end view of a magnetic-field-augmented building in which a magnetic-field augmenter extends under the floor, up a side wall, across a ceiling, and down the other side wall.

Referring now to FIG. 19, magnetic-field-augmented apparatus, or a magnetic-field-augmented building, 230 includes a building, or a building structure, 232, magnetic-field augmenter, or multi-turn augmenter coil, 234, which is symbolized by a dash line, and which extends under a floor 236, up a wall 238A, across a ceiling 240, and down a wall 238B. A magnetic field is produced whose poles are disposed along an axis 242.

Figure 20:
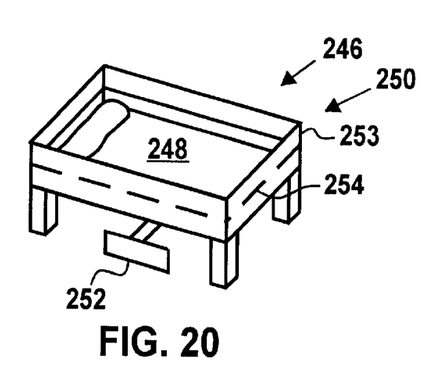
FIG. 20 is a perspective view of a magnetic-field-augmented hospital bed with a magnetic-field-augmented structure surrounding a hospital bed, with a magnetic-field augmenter symbolized by dash lines, and mechanism to raise and lower the magnetic-field-augmented structure.

Referring now to FIG. 20, magnetic-field-augmented apparatus, or a magnetic-field-augmented hospital bed, 246 includes a bed, or a bed structure, 248, a magnetic-field augmenter 250 that is disposed perimetrically around the bed 248, and a lifting mechanism 252 for raising and lowering the magnetic-field augmenter 250. The magnetic-field augmenter 250 includes both a surround structure 253 and an augmenter coil, 254 that is disposed both horizontally and perimetrically in the surround structure 253, as indicated by a dash line.

The magnetic-field augmenter 250, and the surround structure 253 thereof, serves as a bed rail when raised, whether or not a voltage is applied to the augmenter coil 254, and the lifting mechanism 252 lowers the surround structure 253 to provide easy entrance onto, and exit from, the bed 248.

Figure 21:
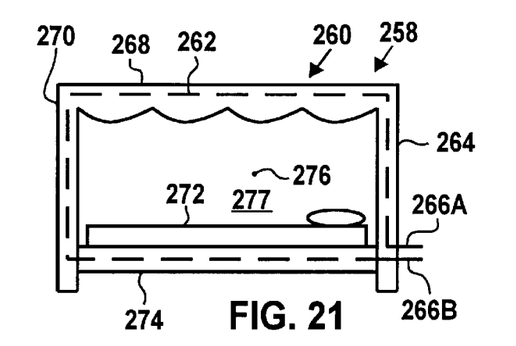
FIG. 21 is a side elevation of a magnetic-field-augmented bed with a magnetic-field augmenter that extends upwardly in a headboard, longitudinally along a canopy toward a footboard, downwardly in the footboard, and under a mattress.

Referring now to FIG. 21, magnetic-field-augmented apparatus, or a magnetic-field-augmented bed, 258 includes a canopy bed, or bed structure, 260 and a magnetic-field augmenter, or multi-turn augmenter coil, 262, as shown by a dash line, that extends upwardly in a headboard 264 from a conductor, or terminal, 266A, longitudinally through a canopy 268 toward a footboard 270, downwardly in the footboard 270, and under a mattress 272 via a bed structure 274 to a conductor, or terminal, 266B. North and south poles are developed along an axis 276. A magnetic-field augmented living area 277 is surrounded by the headboard 264, the canopy 268, the footboard 270, and the mattress 272.

Figure 22:
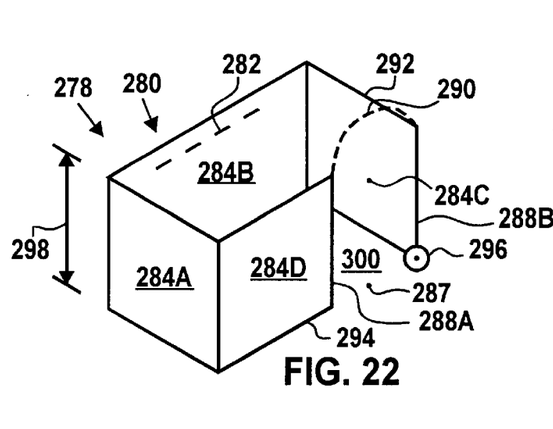
FIG. 22 is a perspective view of a magnetic-field-augmented carrell which can be shaped to substantially enclose a work or sleep area, whose height is sufficient to provide a beneficial D.C. magnetic field for sitting or sleeping, and which can be moved through doors, showing coil jumpers as a dash line.
Figure 23:
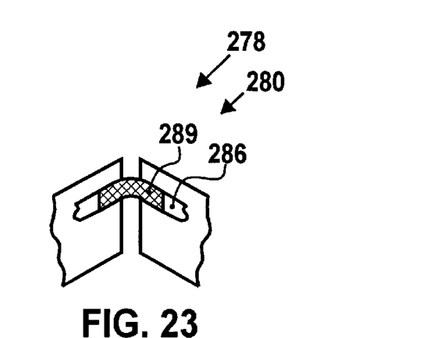
FIG. 23 is a perspective view of a portion of the magnetic-field-augmented carrell of FIG. 22 showing flexible-web hinges that provide both mechanical and electrical interconnection of panels.

Referring now to FIGS. 22 and 23, magnetic-field-augmented apparatus, or a magnetic-field-augmented carrell, 278 includes a foldable carrell, or a carrell structure, 280 and a magnetic-field augmenter, or multi-turn augmenter coil, 282 that is symbolized by a dash line. The magnetic-field augmenter 282 may be constructed of material such as is shown in FIGS. 10 and 11, or by any other suitable means.

The carrell structure 280 includes foldably-hinged panels 284A, 284B, 284C, and 284D, as shown in FIG. 22. A portion of the magnetic-field augmenter 282 is disposed in each of the panels 284A–284D, each panel 284A–284D including a plurality of conductive strips, 286, as shown in FIG. 23. The foldable carrell 280 may be shaped to substantially enclose, except for an opening 287 between ends 288A and 288B, a work space or a sleep area, or any other area in which a beneficial magnetic field is desired.

The conductive strips 286 of adjacent panels, 284A–284D, are interconnected by conductive web strips 289, as shown in FIG. 23. The conductive web strips 289 function as both electrical jumpers and flexible hinges. A bundled-conductor jumper 290 of FIG. 22, which may be located at an upper edge 292 or at a lower edge 294, or both, provides connection of respective ones of the conductive strips 286 between respective ones of the panels 284A–284D, thereby cooperating with the conductive web strips 289 to form the magnetic-field augmenter 282.

Since a magnetic field will flow out of an opening, such as the opening 287, and the resultant magnetic field inside the carrell 280 will lack somewhat in uniformity near the opening 287, a wheel 296 that is pivotally attached to the panel 284D provides means for closing the opening 287 if a more uniform magnetic field is desired.

The magnetic-field-augmented carrell 278 has a height 298 that preferably is short enough to be moved through doors, not shown, and the magnetic-field augmenter 282 is positioned in the height 298 such that a living space 300, is sufficient to provide a beneficial D.C. magnetic field for sitting or sleeping.

Figure 24:
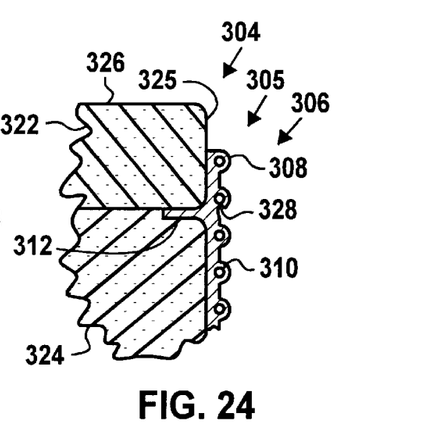
FIG. 24 is a partial elevation, in cross-section, of a magnetic-field augmenter for a bed, made from an extruded strip with multiple conductors enclosed therein.

Referring now to FIG. 24, a magnetic-field augmenter, or mattress augmenter, 304 for a bed, or bed structure, 305 includes a multi-turn augmenter coil 306 that is made from an extruded-plastic strip 308 that includes a plurality of spaced-apart wires 310 therein. Preferably the wires 310 are stranded and are insulated from each other by the plastic material of the extruded-plastic strip 308. The wires 310 are connected into the multi-turn augmenter coil 306 by any suitable means, not an inventive part of the present invention.

Figure 25:
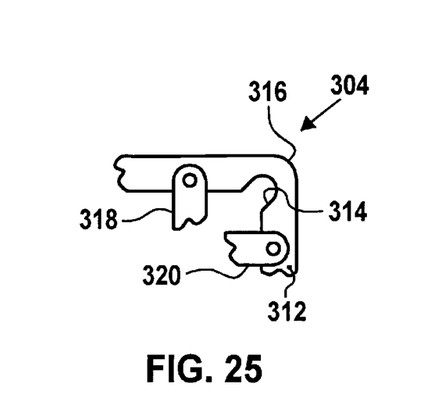
FIG. 25 is a partial top view of the magnetic-field augmenter FIG. 24, showing cross-tie strips that extend both longitudinally and transversely between a mattress and box springs to support the magnetic-field augmenter.

A flange 312 includes notches 314, one shown in FIG. 25, to facilitate bending at corners 316. A plurality of longitudinally-disposed straps 318, and a plurality of transversely-disposed straps 320, one each shown in FIG. 25, extend across a mattress 322 and between the mattress 322 and a box spring 324 of FIG. 24, to support the magnetic-field augmenter 304.

Finally, the mattress 322 of FIG. 24 includes four edges 325, a top surface 326 that is disposed inwardly of the edges 325, and a perimeter 327 that includes the edges 325. And the extruded-plastic strip 308 includes an extruded hook 328 that facilitates anchoring fitted sheets, not shown.

Figure 26:
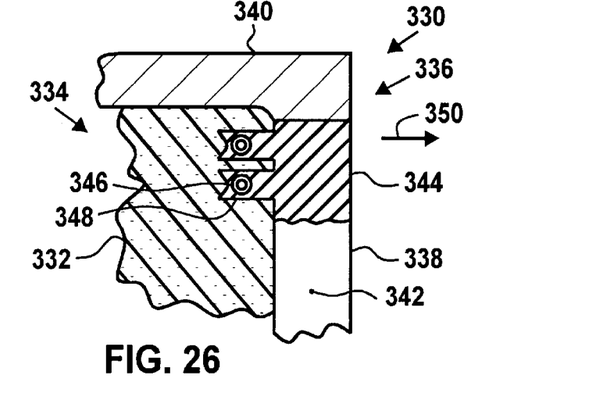
FIG. 26 is a partial elevation, in cross-section, of magnetic-field-augmented mattress, and mold for making same.

Referring now to FIG. 26, magnetic-field-augmented apparatus, or a magnetic-field-augmented mattress 330 includes a foam mattress, or a mattress structure, 332 with a magnetic-field augmenter, or multi-turn augmenter coil, 334 molded in the foam mattress 332.

For manufacturing, a mold 336 includes a surrounding portion 338 and a cover portion 340. The surrounding portion 338 includes a plurality of slots 342 that are perimetrically spaced apart. Plastic locator strips 344 are inserted into the slots 342, a wire 346 is wound perimetrically inside the surrounding portion 338, and clipped into respective ones of resilient clips 348 to form the magnetic-field augmenter 334.

After molding the foam mattress 332, and after removing the foam mattress 332 from the mold 336, the plastic locator strips 344 are removed by pulling them in the direction of an arrow 350, leaving the magnetic-field augmenter 334 molded in the foam mattress 332.

Figure 27:
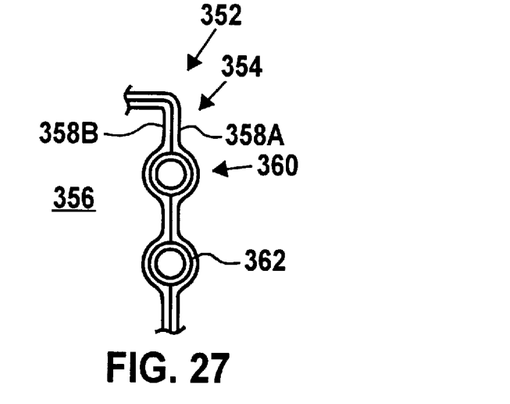
FIG. 27 is a partial elevation, in cross-section, of a magnetic-field-augmented air mattress.

Referring now to FIG. 27, a magnetic-field-augmented apparatus, or a magnetic-field-augmented mattress, 352 includes a mattress, or a mattress structure, 354. The mattress 354 may be of the type wherein water is used in a cavity 356 to provide support, or which may of the type in which air is used. The mattress 354 includes riser portions 358A and 358B. The riser portions 358A and 358B are welded together with a magnetic-field augmenter, or a multi-turn augmenter coil, 360, that is made of a plurality of wires 362, disposed between the riser portions, 358A and 358B.

Figure 28:
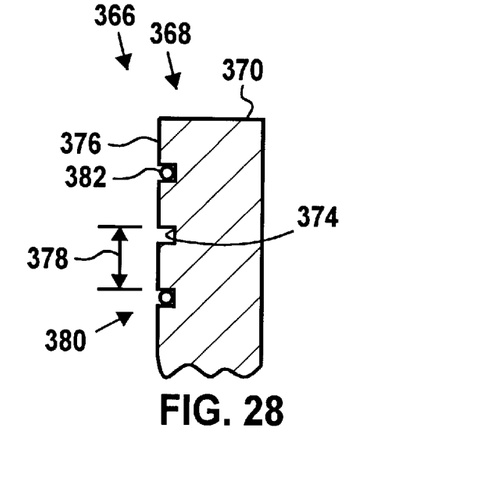
FIG. 28 is a partial elevation, in cross-section, of a magnetic-field-augmented water bed, showing one side rail thereof.
Figure 29:
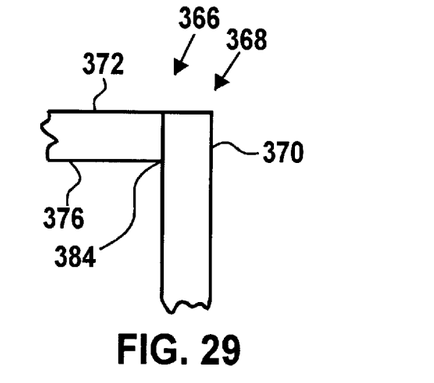
FIG. 29 is a partial top view of the magnetic-field-augmented water bed of FIG. 28, showing one side rail and one end rail.

Referring now to FIGS. 28 and 29, a magnetic-field-augmented bed, or magnetic-field-augmented apparatus, 366 includes a bed, or a bed structure, 368 with side rails 370 and end rails 372, the end rail being shown only in FIG. 29. Grooves 374, which are shown only in FIG. 28, are perimetrically disposed around an inner surface 376 of the rails, 370 and 372, and are spaced apart by a height 378.

A magnetic-field-augmenter, or multi-turn augmenter coil, 380 is formed in the grooves 374 by disposing a wire 382 perimetrically around the bed 368. Preferably, the magnetic-field augmenter 380 is continuously wound, with the wire 382 jumping up one groove 374, or jumping down one groove 374, at one corner 384. However, the grooves 374 may be helically cut to avoid the necessity of jumping from one of the grooves 374 to an other.

Preferably, the wires 382 are permanently retained in the grooves 374 of the side rails 370. Also preferably, the wires 382 are removably retained in the grooves 374 of the end rails 372 to allow for disassembly and shipping. Neither the means for permanently retaining or removably retaining are an inventive part of the present invention.

Figure 30:
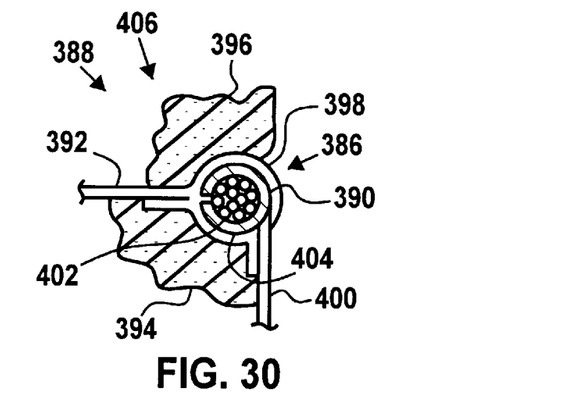
FIG. 30 is a partial elevation, in cross-section, of a magnetic-field augmenter for bed, and the magnetic-field augmenter includes a bundled-loop coil, showing use of the magnetic-field augmenter with a mattress and box spring.

Referring now to FIG. 30, a magnetic-field augmenter 386 for a bed, or a bed structure, 388 includes a multi-turn augmenter coil, or bundled augmenter coil, 390, a supporting web 392 for disposing between a box spring 394 and a mattress 396 of the bed structure 388, a coil tube, or augmenter coil tube, 398, and a skirt 400.

The bundled augmenter coil 390 is made from insulated, and preferably stranded, wire 402 that is continuously looped to form the bundled augmenter coil 390. Alternately, for a higher operating voltage and lower amperage design, the bundled augmenter coil 390 may use a larger number of turns with smaller wire that is both solid and enameled.

The bundled augmenter coil 390 is retained in a bundle by any suitable means, such as a conduit 404. The supporting web 392, the coil tube 398, and the skirt 400 are sewn in a conventional manner from any suitable fabric.

When the magnetic-field augmenter 386 is placed between the mattress 396 and the box spring 394, a magnetic-field-augmented bed, or magnetic-field-augmented apparatus, 406 is provided.

Figure 31:
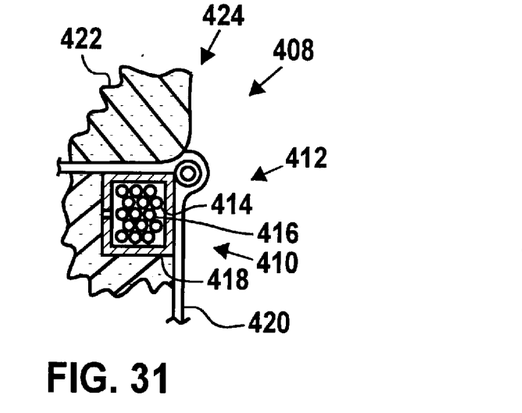
FIG. 31 is a partial elevation, in cross-section of, a magnetic-field-augmented box spring in which the magnetic-field augmenter thereof is in the form of a bundled-loop coil.

Referring now to FIG. 31, magnetic-field-augmented apparatus, or a magnetic-field-augmented bed, 408 includes a box spring, or a box spring structure, 410 and a magnetic-field augmenter 412. The magnetic-field augmenter 412 includes a bundled augmenter coil 414 of continuously looped wire 416 and a bundling conduit 418. The box spring 410 includes a cloth cover 420 that encloses the magnetic-field augmenter 412. When the magnetic-field augmenter is disposed under a mattress 422, the magnetic-field-augmented bed 408 and the mattress 422 cooperate to provide a magnetic-field-augmented bed 424.

Figure 32:
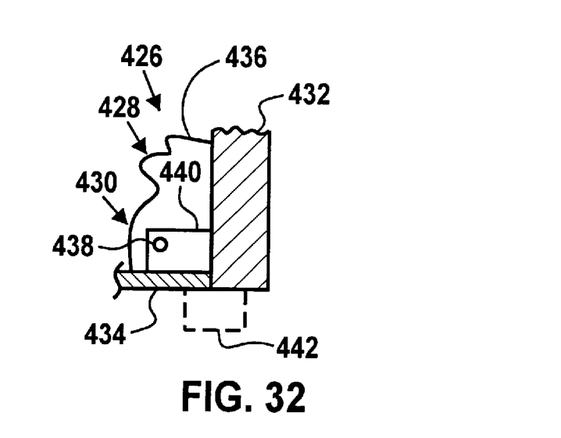
FIG. 32 is a partial elevation, in cross-section, of a magnetic-field-augmented water bed in which the magnetic-field augmenters, which are in the form of a bundled-loop coil, are shown in alternate locations.

Referring now to FIG. 32, magnetic-field-augmented apparatus, or a magnetic-field-augmented water bed 426 includes a water bed, or a water bed structure, 428 and a magnetic-field-augmenter 430. The water bed 428 includes rails 432, a bottom board 434, and a water-bed mattress 436. The magnetic-field augmenter 430 includes a continuously-looped wire 438 with bundled turns that are disposed in a conduit 440. Alternately, the magnetic-field augmenter 430 may be disposed under the water bed 428 as shown by a dash line 442.

Figure 33:
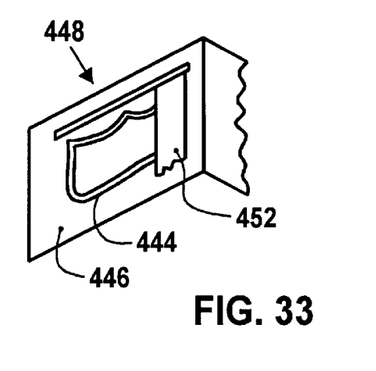
FIG. 33 is a partial perspective view of a wall with a magnetic-field augmenter, in the form of a bundled-loop coil, hanging on a wall and partially covered by drapery.

Referring now to FIG. 33, a magnetic-field augmenter, or wall-hanging augmenter, 444 is hanging on a wall 446 of a room, or room structure, 448. A living space, not shown, that extends outwardly from the wall 446, is magnetic-field-augmented, so that a person, not shown, in front of the magnetic-field augmenter 444 is in a healthful magnetic field.

While the magnetic-field-augmented living space is not identified in FIG. 33, it should be understood that the magnetic-field-augmented living space extends orthogonally from an area defined by the magnetic-field augmenter 444, with poles being disposed along a horizontal axis, not shown. A drape 452 optionally covers the magnetic-field augmenter 444.

Figure 34:
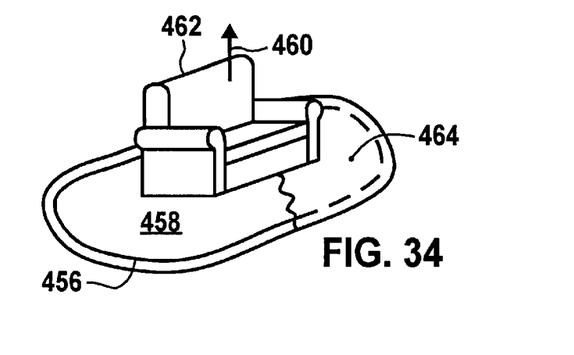
FIG. 34 is a partial perspective view of a room with a magnetic-field augmenter, in the form of a bundled-loop coil, being disposed on the floor, and with seating furniture being disposed inside an area circumscribed by the magnetic-field augmenter.

Referring now to FIG. 34, a magnetic-field augmenter or floor-area augmenter, 456 is disposed on a floor 458. The floor-area augmenter 456 provides a magnetic-field-augmented living space in an area roughly defined by the floor-area augmenter 456, and extends upwardly therefrom with magnetic poles being disposed along a vertical axis 460, so that a person, not shown, sitting in a chair 462 is subjected to a healthful magnetic field. Optionally, the magnetic-field augmenter 456 is incorporated into a magnetic-field augmented area carpet 464.

Figure 35:
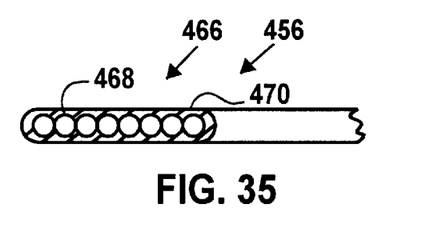
FIG. 35 is a pancake-looped augmenter coil for use in the embodiments of FIGS. 1 and/or 2.

Referring now to FIG. 35, the magnetic-field augmenter 456 of FIG. 34 includes a pancake-looped augmenter coil 466 of wire 468, and a coil cover, or augmenter coil cover, 470 that is bonded to the wires 468.

Figure 36:
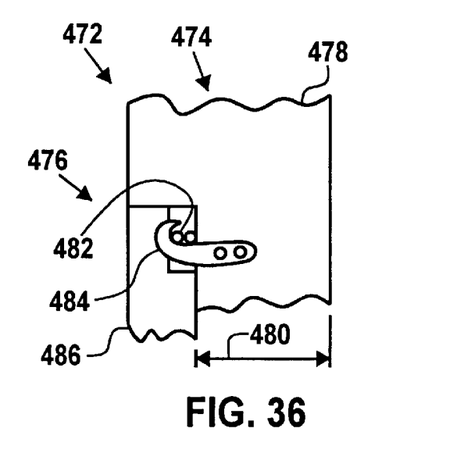
FIG. 36 is a partial elevation of a magnetic-field-augmented building, showing a portion of a notched stud, a bundle-winding hook, two conductors of a bundle disposed on the hook, and a wooden cap strip.

Referring now to FIG. 36, magnetic-field-augmented apparatus, or a magnetic-field-augmented building 472, includes a building, or a building structure, 474 and a magnetic-field augmenter, or bundled augmenter coil, 476.

The building 474 includes studs 478 that are notched to a reduced thickness 480. Wire 482, that is insulated, but that need not be stranded, is wound around the building 474 of FIG. 36, such as is shown in FIG. 16, with the wire 482 being wound into hooks 484 that are nailed to the studs 478.

After completing winding of the wire 482 to form the magnetic-field augmenter 476, cap strips 486 are secured to the studs 478 by any suitable fastening means, thereby restoring a full thickness to the studs 478. The hooks 484 not only secure the wire 482 during winding along the studs 478, but also help in winding the magnetic-field augmenter 476 around inside corners of buildings, such as are shown in FIG. 16.

Continuing to consider FIG. 36, if a magnetically-augmented living space, such as the magnetically-augmented living space 182 of FIG. 14, is assumed to have a height, such as the height 184 of FIG. 14, of 1.52 meters (5.0 feet), then the bundled augmenter coil 476 would be centered within the height 184. That is, the bundled augmenter coil would be disposed 0.76 meters (2.5 feet) from a floor, such as the floor 174 of FIG. 14.

For building structures 474 having more than one story, then an additional bundled augmenter coil 476 is centered in a living space for each story. One or more additional bundled augmenter coils 476 may be disposed between living spaces.

For remodeling existing houses, the bundled augmenter coil 474 may be installed inside one or more rooms, such as the rooms 218A and 218B of FIG. 18. The bundled augmenter coil 476 may be inserted into a slit cut into interior sheetrock, using the hooks 484 at inside corners, and subsequently covering the slit and bundled augmenter coil 476 with a horizontally-disposed trim board, such as a trim board that is commonly called a chair rail.

Figure 37:
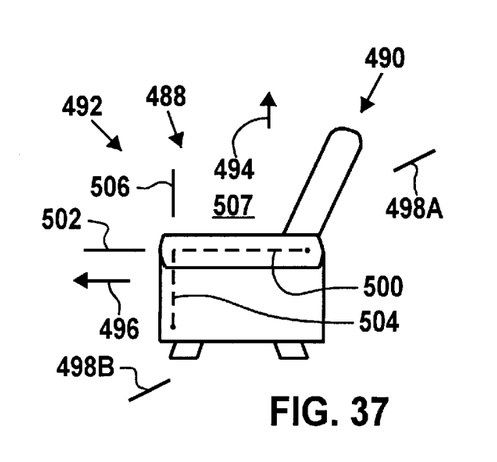
FIG. 37 is an end elevation of magnetic-field-augmented seating furniture, showing bundled conductors that form a two-axis magnetic-field augmenter.

Referring now to FIG. 37, magnetic-field-augmented apparatus, or magnetic-field-augmented seating furniture, 488 includes seating furniture, or seating furniture structure, 490 and a magnetic-field augmenter or two-axis augmenter, 492. The two-axis augmenter 492 produces a magnetic field that is disposed along two axes, one axis with poles along a vertical axis 494, and an other axis with poles along a horizontal axis 496, thereby producing an augmenting field that is distributed upward and backward, forward and downward, and therebetween, as shown by lines 498A and 498B.

That is, the magnetic-field augmenter 492 includes a horizontal coil portion 500 that is disposed along a horizontal plane 502, thereby producing poles along the vertical axis 494, and a vertical coil portion 504 that is disposed along a vertical plane 506, thereby producing poles along the horizontal axis 496, and thereby producing a magnetic-field-augmented living space 507 that is sufficient to engulf a human, not shown, seated in the magnetic-field-augmented seating furniture 488.

Figure 38:
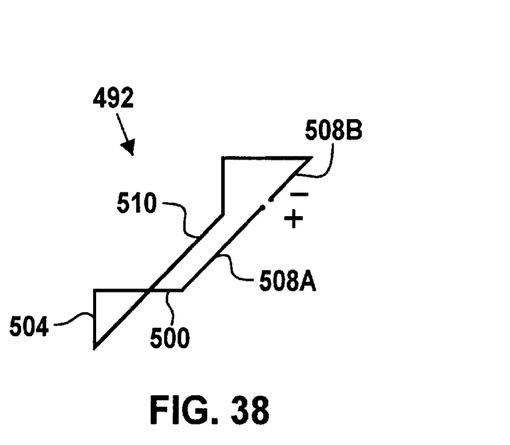
FIG. 38 is a perspective and symbolic view of a magnetic-field-augmenter for the magnetic-field-augmented seating of FIG. 37, illustrating construction of the two-axis magnetic-field-augmenter.

Referring now to FIGS. 37 and 38, but more particularly to FIG. 38, the two-axis augmenter 492 of FIG. 37 is symbolically shown in FIG. 38 as a single-turn coil, but would normally be made as a bundled-conductor coil, as previously described.

The two-axis augmenter 492 includes horizontal coil portions 508A and 508B that are longitudinally disposed, and that are connected to positive and negative potentials, as shown, or to any suitable source of electrical power, two horizontal coil portions 500, only one shown in FIG. 37, that extend forwardly, vertical coil portions 504, only one shown in FIG. 37, that extend downwardly, and a horizontal coil portion 510 that is longitudinally disposed, and that interconnects the coil portions 504.

The coil portions 500, 508A, and 508B, tend to develop a magnetic field whose poles are vertical, as shown by the vertical axis 494 of FIG. 37. In like manner, the portions 504 and 510 tend to develop a magnetic field whose poles are horizontal, as shown by the horizontal axis 496 of FIG. 37. Therefore, the magnetic-field augmenter 492 is a two-axis augmenter.

Figures 39, 40, 41, 42:
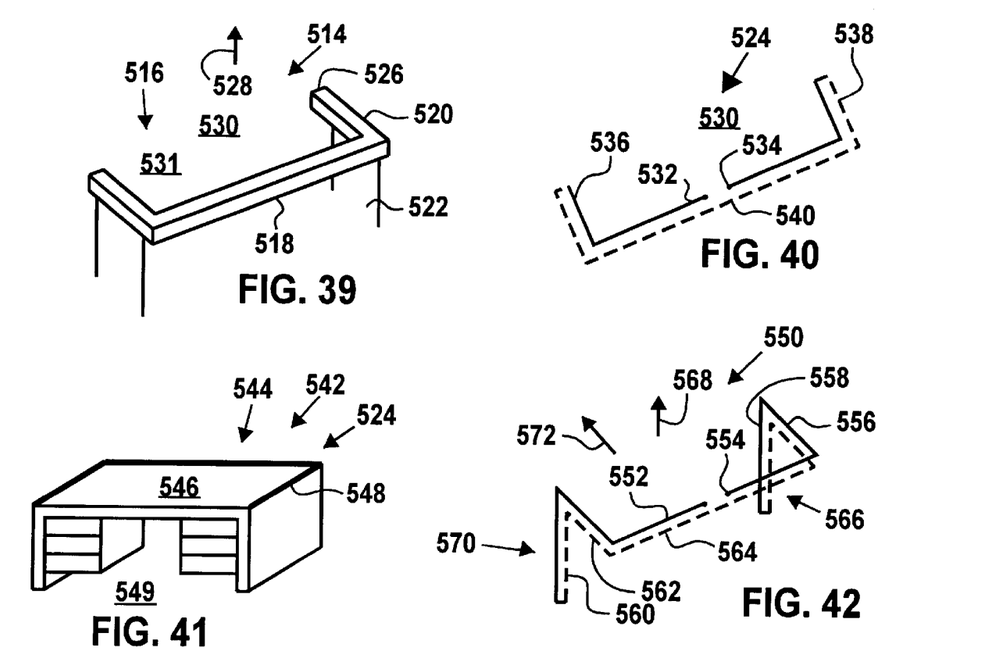
FIG. 39 is a perspective view of a magnetic-field-augmented carrell in the form of a free-standing railing, for providing a magnetic-field-augmented living space when placed behind, and partially around one of more pieces of seating furniture.
FIG. 40 is a schematic, in perspective form of a single-axis magnetic-field augmenter for use in a carrell, such as the carrell of FIG. 39, showing shielded return conductors in dash lines.
FIG. 41 is a perspective drawing of magnetic-field-augmented desk that includes the single-axis magnetic-field augmenter of FIG. 40, showing a general location of the U-shaped augmenter by means of heavier outlines of the desk top.
FIG. 42 is a schematic, in perspective form of a two-axis magnetic-field augmenter that may be used to construct various magnetic-field-augmented apparatus, such as a carrell similar to that of FIG. 39, showing shielded return conductors in dash lines.

Referring now to FIG. 39, magnetic-field-augmenter apparatus, or free-standing augmented railing, 514 includes a U-shaped railing, or a free-standing structure, 516. The U-shaped railing 516 includes a longitudinal back portion 518, a pair of side portions, 520, and four legs 522. A magnetic-field augmenter, U-shaped augmenter, or single-axis open-sided augmenter, 524, shown only in FIG. 40, is disposed within the U-shaped railing 516, and extends generally to each end 526 of the U-shaped railing 516.

The free-standing augmented railing 514 produces a magnetic field whose poles are generally disposed along a vertical axis 528, but since the magnetic-field augmenter 524 of FIG. 40 does not extend across the ends 526, an open side 530 of FIG. 39 reduces reluctance of the flow path, so that magnetic flux spills out the open side 530, thereby providing a magnetic-field augmented living space 531 that extends in front of the open side 530 and well as inside a space partially enclosed by the U-shaped railing 516.

Referring now to FIG. 40, the U-shaped augmenter 524 includes a pair of active back portions 532 with terminals 534 which may be connected to a source of electrical power, a pair of active side portions 536, a pair of magnetically-shielded side portions 538, and a magnetically-shielded back portion 540. Magnetic shielding can be achieved by the use of soft iron sheets, or by any suitable means, not an inventive part of the present invention.

By shielding the portions 538 and 540, the magnetic-field augmenter 524 can be open on the side 530 of FIGS. 39 and 40 and still produce a magnetic field whose poles are generally vertical, as shown by the axis 528 of FIG. 39.

Therefore, the U-shaped augmenter 524 allows construction of U-shaped magnetic-field augmented apparatus, such as the free-standing augmented railing 514, whose healthful magnetic field is disposed generally along the vertical axis 528, but whose healthful field also spills over forwardly, thereby providing a magnetic-field-augmented living space that is larger than an area enclosed by the magnetic-field augmenter.

Referring now to FIG. 41, magnetic-field-augmented apparatus, or a magnetic-field-augmented desk, 542 includes a desk, or a desk structure, 544 and the magnetic-field augmenter or U-shaped augmenter, 524 of FIG. 40. The desk 544 includes a top 546, and the location of the U-shaped augmenter 524 is symbolized by heavier lines along three of four edges 548 of the top 546.

Since the U-shaped augmenter 524 is open-sided, although the poles of the magnetic-field developed thereby are generally vertical, it is easy to see that the magnetic field will flow forward, thereby providing a magnetic-field-augmented living space 549 that will engulf a person, not shown, who is using the desk 544.

Referring now to FIG. 42, a magnetic-field augmenter, or two-axis open-coil augmenter, 550 includes a pair of active longitudinal portions 552 that are horizontally disposed, each having a terminal 554 that may be connected to a source of electrical power, a pair of active transverse portions 556 that are horizontally disposed, a pair of active vertical portions 558, a pair of magnetically-shielded vertical portions 560, a pair of magnetically-shielded traverse portions 562, and a magnetically-shielded longitudinal portion 564.

The active portions 552 and 556 form a horizontally-disposed coil portion 566 whose poles are generally vertical, as shown by a vertical axis 568. In like manner, the active vertical portions 558 form a vertically-disposed coil portion 570 whose poles are generally horizontal, as shown by a horizontal axis 572.

Referring now to FIGS. 40 and 42, both of the magnetic-field augmenters, 524 and 550 are open-sided, both include turns in which portions of turns thereof double back on themselves, and both magnetically shield the portions of the turns that double back. The magnetic-field augmenter 524 produces a magnetic field whose axes are disposed as shown by the vertical axis 528 of FIG. 39, and the magnetic-field augmenter 550 of FIG. 42 produces magnetic fields whose axes are disposed along two axes, the vertical axis 568 and the horizontal axis 572.

Figure 43:
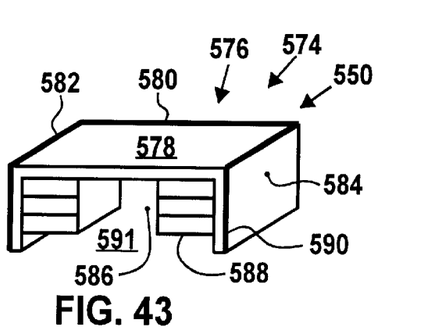
FIG. 43 is a perspective drawing of a magnetic-field-augmented desk that includes the two-axis magnetic-field augmenter of FIG. 42, showing a general location of the two-axis augmenter by heavier outlines that enclose three sides of the desk top, and that extends downward on opposite sides of a user's legs.

Referring now to FIG. 43, magnetic-field-augmented apparatus, or a magnetic-field-augmented desk, 574 includes a desk, or desk structure, 576 and the two-axis open-coil augmenter 550 of FIG. 42. The desk 576 includes a top 578 having a front edge 580 and a pair of side edges 582, a pair of panel-type legs 584, and a kneehole 586 that is disposed between a pair of drawer units 588.

The magnetic-field augmenter 550 of FIG. 42 is disposed generally along the back edge 580, forwardly along the side edges 582, and downwardly along corner edges 590, as shown by heavier lines.

Since the magnetic-field augmenter 550 of FIG. 42 produces magnetic-fields that are disposed both horizontally and vertically, as shown by axes 568 and 572, it is obvious a magnetic-field-augmented living space 591 of FIG. 43 will provide an augmented magnetic field for hands, arms, and head, not shown, of a person that may be disposed generally above the top 578, for legs and feet, not shown, that may be disposed generally in the kneehole 586, and for a torso, not shown, of a person that is disposed in behind the magnetic-field-augmented desk 574.

Figure 44:
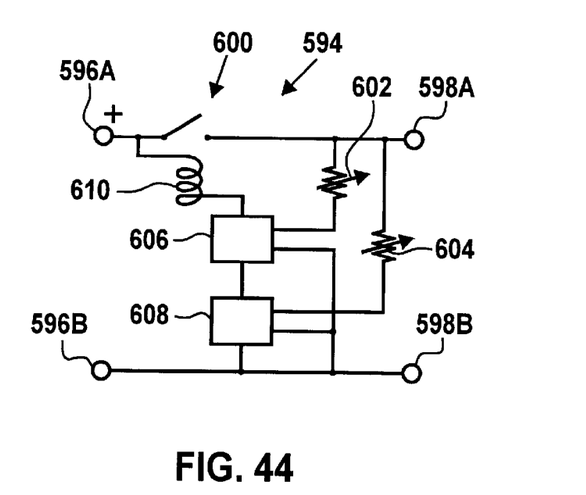
FIG. 44 is a schematic drawing of a protective device for shutting down a magnetic-field augmenter if a loose connection increases a resistance thereof, or if a short decreases the resistance thereof.

Referring now to FIG. 44, a protective device 594 includes input terminals 596A and 596B for connection to a source of electrical power such as the one shown in FIG. 5, augmenter terminals 598A and 598B for connection to magnetic-field augmenters, such as those taught herein, a normally-open relay, 600, a lower-limit resistance reference 602, a higher-limit resistance reference 604, a lower-limit comparator 606, and a higher-limit comparator 608.

In operation, when a resistance across the augmenter terminals 598A and 598B is within limits set by the resistance references, 602 and 604, it indicates that there are neither loose electrical connections nor shorts in the augmenter, not shown, nor any loose connection between the augmenter and the protective device 594.

At this time, the comparators, 606 and 608, which are in series, communicate a coil 610 of the relay 600 to the input terminal 596A, thereby closing a circuit that energizes the coil 610 and closes the relay 600. However, if the resistance across the augmenter terminals 598A and 598B is below the lower-limit resistance reference 602, or if the resistance across the augmenter terminals 598A and 598B exceeds a higher-limit resistance reference 604, the circuit from the coil 610 to the input terminal 596A is broken, thereby opening the relay 600, and shutting down the augmenter that is attached to the augmenter terminals, 598A and 598B.

While reference has been made herein to mattresses and box springs, more generically, and as used in the claims: a mattress and a box spring together form a sleep set; the mattress is a sleep unit, and the box spring is a sleep unit; the mattress is an upper sleep unit, or resilient sleep unit; and the box spring, whether or not it actually includes springs or is only a padded box, is a lower sleep unit.

Further, while reference has been made to top surfaces of mattresses, or upper sleep units, as used in the claims, lower sleep units, or box springs, also include top surfaces. A living space is provided above a top surface of a lower sleep unit, even though an upper sleep unit may be interposed between the top surface of the lower sleep unit and the living space. And, both sleep units include bottom surfaces as well as top surfaces.

As shown and described above, and as defined herein, augmenting, or supplementing the earth's magnetic field means applying to a person's entire body, or to an entire living thing, a magnetic field that adds to the earth's magnetic field.

If a magnetic field were provided in which orientation of the magnetic poles reversed in different portions of a living space, then in some portions of the living space, rather than augmenting the earth's magnetic field, the added magnetic field would reduce, or even cancel, the earth's magnetic field.

Therefore, as shown and described herein, an augmenting field is unipolar in the living space. That is, as defined herein, a magnetic field is unipolar if, throughout the living space, the magnetic poles of the added magnetic field do not reverse.

While augmenting the earth's magnetic field has been emphasized for providing a healthful environment, the primary thrust of the present invention is immersion of the entire body in a magnetic field whose total magnitude is greater than the earth's magnetic field whether or not the body of the living thing is shielded from the earth's magnetic field.

Further, while constant D.C. magnetic fields have been discussed, and while they are deemed to be preferable for use in augmenting the earth's magnetic field, varying or pulsed D.C. magnetic fields, or A.C. magnetic fields whose frequencies may be discovered to be beneficial to life, may be used to practice the present invention.

Still further, although the use of augmenters has focused on providing a more healthful living environment, as opposed to providing therapeutic apparatus and method, the augmenters taught herein may be used, at various gauss intensities, for therapeutic treatment by immersing a patient's entire body, or an entire living thing, into a living area which may be a bed, a special therapeutic device, a portion of a room, a room, or an entire building, for periods of time that may range from a portion of an hour to days or even weeks.

While specific apparatus and method have been disclosed in the preceding description, it should be understood that these specifics have been given for the purpose of disclosing the principles of the present invention, and that many variations thereof will become apparent to those who are versed in the art. Therefore, the scope of the present invention is to be determined by the appended claims, and without regard to any numbers that may be parenthetically inserted in any of the claims.

What is claimed is:

1. A method for preventing at least some of the deleterious effects of A.C. magnetic fields, which method comprises:
   a) providing a living space having a length, a width, and a height; and
   b) supplementing earth's magnetic field in said living space with a unipolar D.C. magnetic field that is substantially constant.

2. A method as claimed in claim 1 in which said D.C. magnetic field comprises a D.C. magnetic field whose time-weighted average is between about 1.0 and 5.0 gauss.

3. A method as claimed in claim 1 in which said supplementing step comprises disposing an augmenter coil around at least a portion of a perimeter of said living space; whereby magnetic poles of said supplementing magnetic field are disposed upwardly and downwardly.

4. A method as claimed in claim 1 in which said supplementing step comprises random bundling turns of an augmenter coil.

5. A method as claimed in claim 1 in which said supplementing step comprises:
   a) using an augmenter coil that is essentially devoid of a magnetic core; and
   b) spacing turns of said augmenter coil from each other by spaces that exceed 5.08 mm (0.20 inches).

6. A method for healthful living, which method comprises:
   a) disposing one's entire body into a living space having a length, a width, and a height;
   b) supplementing earth's magnetic field in said living space with a unipolar D.C. magnetic field whose poles are oriented upwardly and downwardly; and
   c) performing a life activity in said living space during said supplementing step.

7. A method for supplementing earth's magnetic field as an integral part of normal sleep, which method comprises:
   a) providing a bed having a sleep unit with a living space above a top surface, said living space having a length, a width, and a height that is sufficient to envelop a person lying on said sleep unit;
   b) supplementing said earth's magnetic field in said living space with a unipolar D.C. magnetic field that is substantially constant during at least a period of time wherein said bed is used for said normal sleep; and
   c) said supplementing step comprises disposing a magnetic-field-augmenter, in its entirety, within a range of positions that extends from about said top surface to a floor beneath said bed.

8. A method for applying a supplementary magnetic field to a living thing, which method comprises:
   a) providing a living space in which said living things is able to stand and move around;
   b) disposing said living thing into said living space;
   c) retaining said living thing in said living space for a period of time that exceeds four hours; and
   d) supplementing earth's magnetic field in said living space with a unipolar magnetic field whose poles are disposed upwardly and downwardly.

9. A method for magnetic-field augmenting a living space of a bed, said bed having a sleep unit with a top surface that is disposed intermediate of four edges of said sleep unit, and said living space being disposed above said top surface, which method comprises:
   a) disposing an augmenter coil in a pattern that generally conforms to said edges; and
   b) supportingly positioning said augmenter coil in its entirety, within a range of positions that extends from about said top surface to a floor beneath said bed.

10. A method for providing a magnetic-field-augmented living space that is relocatable, which method comprises:
    a) disposing a free-standing support around a portion of a perimeter of a selected living space;
    b) leaving an access opening between ends of said free-standing support; and
    c) attaching an augmenter coil to free-standing support.

11. A method as claimed in claim 10 in which said attaching of said augmenter coil to said free-standing support comprises:
    a) disposing a first portion of said augmenter coil between said ends of said free-standing support;
    b) doubling back a second portion of said augmenter coil between said ends of said free-standing support; and
    c) magnetically shielding said second portion.

12. A method as claimed in claim 10 in which said method further comprises leaving said opening free of electrical communication between said ends.

13. A method as claimed in claim 10 in which said method further comprises:
    a) folding said free-standing support;
    b) relocating said free-standing support; and
    c) unfolding said free-standing support.

14. A method for magnetic-field augmenting a living space, which method comprises:
    a) generating an augmenting magnetic field;
    b) generating a first portion of said augmenting magnetic field with poles that are disposed along a first axis; and
    c) generating a second portion of said augmenting magnetic field with poles that are disposed along a second axis that is at an angle to said first axis.

15. A method as claimed in claim 14 in which said generating steps comprise:
   a) disposing a first portion of an augmenter coil orthogonal to said first axis; and
   b) disposing a second portion of said augmenter coil orthogonal to said second axis.

16. A method as claimed in claim 14 in which said method further comprises;
   a) doubling back one-half of one turn of said augmenter coil against an other half of said one turn; and
   b) magnetically shielding said doubled-back one-half turn.

17. Magnetic-field-augmented apparatus which comprises:
   means, comprising a sleep unit with a perimeter that extends around four edges, and with a top surface disposed intermediate of said perimeter, for providing a living space above said top surface;
   an augmenter coil generally conforming to said perimeter; and
   means for supportively positioning said augmenter coil in a range of positions between about said top surface and a floor.

18. Magnetic-field-augmented apparatus as claimed in claim 17 in which said means for positioning said augmenter coil comprises means for making said augmenter coil an integral part of said sleep unit.

19. Magnetic-field-augmented apparatus as claimed in claim 17 in which:
   said apparatus comprises a bed structure and an other sleep unit that is disposed intermediate of the first said sleep unit and said bed structure; and
   said means for supportively positioning said augmenter coil comprises means for insertion between said sleep units.

20. Magnetic-field-augmented apparatus as claimed in claim 17 in which said means for supportively positioning said augmenter coil comprises means for interconnecting portions of said augmenter coil on two opposite sides of said perimeter.

21. Magnetic-field-augmented apparatus as claimed in claim 17 in which said means for supportively positioning said augmenter coil comprises a web that is disposed inwardly of said perimeter and that is operatively attached to said augmenter coil.

22. Magnetic-field-augmented apparatus as claimed in claim 17 in which:
   said apparatus comprises a bed structure; and
   said means for supportively positioning said augmenter coil comprises said bed structure.

* * * * *